United States Patent
Matsumoto et al.

(10) Patent No.: US 9,506,012 B2
(45) Date of Patent: Nov. 29, 2016

(54) FRAGRANCE COMPOSITION

(71) Applicant: KAO CORPORATION, Tokyo (JP)

(72) Inventors: Tomotaka Matsumoto, Tokyo (JP);
Takashi Aoki, Wakayama (JP);
Takahiro Hirose, Chiba (JP); Shoichi Tahara, Chiba (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 14/894,448

(22) PCT Filed: May 20, 2014

(86) PCT No.: PCT/JP2014/002654
§ 371 (c)(1),
(2) Date: Nov. 27, 2015

(87) PCT Pub. No.: WO2014/192250
PCT Pub. Date: Dec. 4, 2014

(65) Prior Publication Data
US 2016/0115423 A1    Apr. 28, 2016

(30) Foreign Application Priority Data

May 27, 2013 (JP) .................................. 2013-111115

(51) Int. Cl.
| | | |
|---|---|---|
| *C11B 9/02* | (2006.01) | |
| *C11D 3/50* | (2006.01) | |
| *C11D 3/26* | (2006.01) | |
| *A61Q 5/02* | (2006.01) | |
| *A61Q 19/10* | (2006.01) | |
| *A61K 8/40* | (2006.01) | |
| *C11B 9/00* | (2006.01) | |
| *C11D 3/00* | (2006.01) | |

(52) U.S. Cl.
CPC ................. *C11B 9/003* (2013.01); *A61K 8/40* (2013.01); *A61Q 5/02* (2013.01); *A61Q 19/10* (2013.01); *C11D 3/001* (2013.01); *C11D 3/26* (2013.01); *C11D 3/50* (2013.01)

(58) Field of Classification Search
None
See application file for complete search history.

(56) References Cited

U.S. PATENT DOCUMENTS

| | | |
|---|---|---|
| 2008/0200359 A1 | 8/2008 | Smets et al. |
| 2008/0200363 A1 | 8/2008 | Smets et al. |
| 2009/0048351 A1 | 2/2009 | Smets et al. |
| 2010/0152264 A1 | 6/2010 | Herrmann et al. |
| 2010/0331190 A1 | 12/2010 | Smets et al. |

FOREIGN PATENT DOCUMENTS

| | | |
|---|---|---|
| GB | 1 210 866 | 11/1970 |
| JP | 47-440 | 1/1972 |
| WO | 95/11231 | 4/1995 |
| WO | 2008/100625 | 8/2008 |
| WO | 2008/142591 | 11/2008 |

OTHER PUBLICATIONS

Motoichi Indo, "Synthetic perfume," Chemistry and goods information, 2005, Total 8 pages, (With partial translation).
Niko Radulovic, et al., "A novel toxic alkaloid from poison hemlock (*Conium maculatum* L., *Apiaceae* ): Identification, synthesis and antinociceptive activity," Food and Chemical Toxicology, vol. 50, 2012, pp. 274-279, XP055131855.
International Search Report Issued Aug. 11, 2014 in PCT/JP14/02654 Filed May 20, 2014.

*Primary Examiner* — Michael Barker
(74) *Attorney, Agent, or Firm* — Oblon, McClelland, Maier & Neustadt, L.L.P.

(57) ABSTRACT

The present invention provides a method of using, as a fragrance component, a compound that is excellent in fragrance retention and that has green floral and fruity like odors, which are useful as fragrances, and a fragrance composition with sweetness and voluminousness containing the compound. The present invention relates to a fragrance composition containing 2-n-pentyl cyclopentanone oxime and a method of using 2-n-pentyl cyclopentanone oxime as a fragrance component.

20 Claims, No Drawings

FRAGRANCE COMPOSITION

FIELD OF THE INVENTION

The present invention relates to a fragrance composition.

BACKGROUND OF THE INVENTION

Fragrance is an important element that creates, for example, preference, a sense of luxury, a sense of ease, and expectations for the effect for products and the like. Furthermore, a distinctive fragrance provides a product differentiation effect and the capacity for attracting customers. On the other hand, in order to control, for example, a long-lasting property and balance of fragrance, generally, a fragrance is imparted to a product using a fragrance composition in which a plurality of fragrance materials are mixed together. It is required for the fragrance materials composing the fragrance composition to be highly harmonious with other fragrance materials.

Stemone (Givaudan), 5-methyl-3-heptanone oxime having a green odor, Labienoxime (Givaudan), 2,4,4,7-tetramethyl-6,8-nonadiene-3-one oxime, and Buccoxime (Symrise), 1,5-dimethyl-bicyclo[3.2.1]octan-8-one oxime having fruity and herbal odors are known as fragrance materials with an oxime structure (see "Gosei Koryo, Kagaku to Shohin Chishiki" (Synthetic Perfumes, Chemistry and Commodity Knowledge), authored by Genichi Indo, Enlarged and Revised Edition, 2005, pp. 280, 729, and 730).

Furthermore, as a fragrance material with a cyclopentane ring structure, Delphone (Firmenich), amyl cyclopentanone, is known to have jasmine-like fruity and floral odors (see "Gosei Koryo, Kagaku to Shohin Chishiki" (Synthetic Perfumes, Chemistry and Commodity Knowledge), authored by Genichi Indo, Enlarged and Revised Edition, 2005, pp. 280, 729, and 730).

Moreover, N. Radulovic, et al., Food and Chemical Toxicology (2012, pp. 50, 274-279), describes a method of synthesizing a new alkaloid via 2-pentyl cyclopentanone oxime with a cyclopentane ring structure but does not describe the odor of the 2-pentyl cyclopentanone oxime.

Very roughly speaking, fragrance materials have similar fragrance notes when they have similar structures to each other, but there are many exceptions. Particularly, when a plurality of substituents are combined to change the fragrance note, it is difficult to predict how the fragrance note will change and it also is difficult to predict the harmonicity with other fragrance materials.

SUMMARY OF THE INVENTION

Therefore, with the foregoing in mind, it is an object of the present invention to provide a fragrance composition containing 2-n-pentyl cyclopentanone oxime.

DETAILED DESCRIPTION OF THE INVENTION

The present invention is intended to provide a method of using, as a fragrance component, a compound that has green floral and fruity like odors and is excellent in fragrance retention, and a fragrance composition that contains the compound and has sweetness and voluminousness.

The present inventors found that the use, as a fragrance component, of a specific oxime compound with a cyclopentane ring structure makes it possible to obtain a fragrance composition with sweetness and voluminousness, which has green floral and fruity like odors, is excellent in fragrance retention, and can enhance the sweetness and increase the voluminousness by being blended with another fragrance. This allowed the present invention to be completed.

The present invention provides a fragrance composition containing 2-n-pentyl cyclopentanone oxime.

The present invention can provide a method of using, as a fragrance component, 2-n-pentyl cyclopentanone oxime that has green floral and fruity like odors and is excellent in fragrance retention, and a fragrance composition with sweetness and voluminousness containing 2-n-pentyl cyclopentanone oxime.

<Fragrance Composition>

The fragrance composition of the present invention contains 2-n-pentyl cyclopentanone oxime.

[Chem.1]

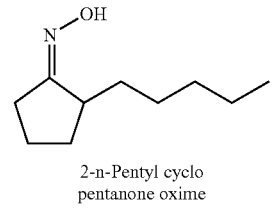

2-n-Pentyl cyclo
pentanone oxime

The amount of the 2-n-pentyl cyclopentanone oxime contained in the fragrance composition of the present invention is preferably 0.01 to 99 mass %, more preferably 0.1 to 50 mass %, and further preferably 0.3 to 25 mass %, from the view points of enhancing the sweetness and increasing the voluminousness of the fragrance composition.

The fragrance composition of the present invention can contain an oil, which itself has no odor, to be used as a base that allows 2-n-pentyl cyclopentanone oxime and other fragrance materials to be contained therein. Such an oil allows a fragrance component to be mixed uniformly, to be easily mixed into a product, and to be easily provided with a suitable intensity of fragrance. Examples of the oil include polyhydric alcohols such as ethylene glycol, propylene glycol, butylene glycol, and dipropylene glycol, esters such as isopropyl myristate, dibutyl adipate, and diethyl sebacate, hydrocarbons such as liquid paraffin and squalane, and surfactants such as polyoxyethylene alkyl ether and sorbitan fatty acid ester.

Among them, from the viewpoints of the solubility of all the fragrance components and the long-lasting property and diffusibility of the odor, the oil is preferably polyhydric alcohol or ester, more preferably dipropylene glycol or isopropyl myristate. The amount of such an oil to be contained in the fragrance composition is preferably 0.01 to 95 mass %, more preferably 1 to 90 mass %, and further preferably 5 to 80 mass %, from the viewpoints of enhancing the sweetness and increasing the voluminousness of the fragrance composition as well as the viewpoint of enhancing the long-lasting property and diffusibility of the odor.

Since the fragrance composition of the present invention contains 2-n-pentyl cyclopentanone oxime, it has green floral and fruity like odors and is excellent in fragrance retention. Furthermore, the fragrance composition of the present invention can contain, in addition to the 2-n-pentyl cyclopentanone oxime, another fragrance component that is commonly used or a blended fragrance with a desired composition as another fragrance and thereby it can be provided with an odor of, for example, a citrus tone, a floral tone, a fruity tone, a herbal tone, a spicy tone, a green tone, a woody tone, a balsamic tone, an aldehydic tone, a minty tone, an aromatic tone, an earthy tone, a mossy tone, a honey tone, a leather tone, an animalic tone, an amber tone, and/or a musky tone.

In the fragrance composition of the present invention, another fragrance that can be used in combination with 2-n-pentyl cyclopentanone oxime is preferably at least one selected from the group consisting of fragrances having respective fragrance notes of a citrus tone, a floral tone, a fruity tone, a herbal tone, a spicy tone, a green tone, a woody tone, a balsamic tone, an aldehydic tone, a minty tone, an aromatic tone, an earthy tone, a mossy tone, a honey tone, a leather tone, an animalic tone, an amber tone, and a musky tone. Particularly from the viewpoints of enhancing the sweetness and increasing the voluminousness of the fragrance composition, it is more preferably at least one selected from fragrances having respective fragrance notes of a citrus tone, a floral tone, a fruity tone, a spicy tone, a green tone, and a woody tone, and further preferably a fragrance having a fragrance note of a floral tone.

In the fragrance composition of the present invention, another fragrance that can be used in combination with 2-n-pentyl cyclopentanone oxime is preferably at least one selected from the group consisting of hydrocarbons, alcohols, phenols, aldehydes, ketones, acetals, ethers, esters, carbonates, lactones, oximes, nitriles, Schiff bases, amides, nitrogen-containing compounds, sulfur-containing compounds, natural essential oils, and natural extracts. Particularly, from the view points of enhancing the sweetness and increasing the voluminousness by being blended with 2-n-pentyl cyclopentanone oxime, it is more preferably at least one selected from the group consisting of alcohols, aldehydes, ketones, acetals, ethers, esters, lactones, Schiff bases, nitrogen-containing compounds, sulfur-containing compounds, natural essential oils, and natural extracts.

In the present invention, the "plural notation" of each fragrance denotes a single compound or a mixture of at least two compounds.

Examples of hydrocarbons include limonene, alpha-pinene, beta-pinene, terpinene, pcymene, cedrene, longifolene, valencene, camphene, and myrcene.

Examples of alcohols include aliphatic alcohols, terpene-based alcohols, and aromatic alcohols.

Examples of aliphatic alcohols include prenol, trans-2-hexenol, cis-3-hexenol, 2,6-dimethylheptanol, 1-octen-3-ol, 2,6-nonadienol, 3,6-nonadienol, Undecavertol (Trade Name of Givaudan, 4-methyl-3-decene-5-ol), 2,4-dimethyl-3-cyclohexene-1-methanol, iso cyclo geraniol, o-tert-butylcyclohexanol, p-tert-butylcyclohexanol, Mayol (Trade Name of Firmenich, 4-(1-methylethyl)-cyclohexanemethanol), Amber Core (Trade Name of Kao Corporation, 1-(2-tert-butyl cyclohexyloxy)-2-butanol), Timberol (Trade Name of Symrise, 1-(2,2,6-trimethylcyclohexyl)hexan-3-ol), Sandalmysore Core (Trade Name of Kao Corporation, 2-methyl-4-(2,2,3-trimethyl-3-cyclopenten-1-yl)-2-buten-1-ol), Bacdanol (Trade Name of IFF, 2-ethyl-4-(2,2,3-trimethyl-3-cyclopenten-1-yl)-2-buten-1-ol), Florosa (Trade Name of Givaudan, 4-methyl-2-(2-methylpropyl)tetrahydro-2H-4-pyranol), and Magnol (Trade Name of Kao Corporation, an isomer mixture containing, for example, (4-ethyl-bicyclo[2.2.1]hept-2-yl)cyclohexanol and (2-ethyl-bicyclo[2.2.1]hept-7-yl)cyclohexanol). Trans-2-hexenol, 2,4-dimethyl-3-cyclohexene-1-methanol, iso cyclo geraniol, Mayol, Magnol, and Florosa are preferable from the viewpoints of enhancing the sweetness and increasing the voluminousness by being blended with 2-n-pentyl cyclopentanone oxime.

Examples of terpene-based alcohols include citronellol, hydroxycitronellol, linalool, dihydrolinalool, tetrahydrolinalool, ethyllinalool, geraniol, nerol, tetrahydrogeraniol, myrcenol, dihydromyrcenol, tetrahydromyrcenol, ocimenol, terpineol, menthol, borneol, fenchyl alcohol, farnesol, nerolidol, and cedrol. Citronellol, hydroxycitronellol, linalool, dihydrolinalool, tetrahydrolinalool, ethyllinalool, geraniol, nerol, tetrahydrogeraniol, myrcenol, dihydromyrcenol, tetrahydromyrcenol, terpineol, and nerolidol are preferable from the viewpoints of enhancing the sweetness and increasing the voluminousness by being blended with 2-n-pentyl cyclopentanone oxime.

Examples of aromatic alcohols include benzyl alcohol, styralyl alcohol, phenethyl alcohol, cumin alcohol, dimethyl phenyl ethyl carbinol, cinnamic alcohol, Phenyl Hexanol (Trade Name of Kao Corporation), Pamplefleur (Trade Name of IFF, 4-phenylpentanol), and Majantol (Trade Name of Symrise, 2,2-dimethyl-3-(3-methylphenyl)propanol). Benzyl alcohol, styralyl alcohol, phenethyl alcohol, dimethyl phenyl ethyl carbinol, Phenyl Hexanol, Pamplefleur, and Majantol are preferable from the viewpoints of enhancing the sweetness and increasing the voluminousness by being blended with 2-n-pentyl cyclopentanone oxime.

Examples of phenols include anethole, guaiacol, eugenol, and isoeugenol.

Examples of aldehydes include aliphatic aldehyde, terpene aldehyde, and aromatic aldehyde as in the case of the aforementioned alcohols. All the aldehydes in which only the alcohol group of the fragrance component alcohols has been converted to aldehyde group are included in the examples of the fragrance components.

Examples of other aldehydes include Aldehyde C-6 (Trade Name of Kao Corporation, hexanal), Aldehyde C-8 (Trade Name of Kao Corporation, octanal), Aldehyde C-9 (Trade Name of Kao Corporation, nonanal), Aldehyde C-10 (Trade Name of Kao Corporation, decanal), Aldehyde C-11 Undecyl (Trade Name of Kao Corporation, undecanal), Aldehyde C-111 LEN (Trade Name of Kao Corporation, 10-undecenal), 2-methyldecanal, Aldehyde C-12 Lauryl (Trade Name of Kao Corporation, dodecanal), Aldehyde C-12 MNA (Trade Name of Kao Corporation, 2-methylundecanal), cis-4-decenal, trans-4-decenal, Floral Super (Trade Name of IFF, 4,8-dimethyl-4,9-decadienal), Pollenal II (Trade Name of Kao Corporation, 2-cyclohexylpropanal), Myrac Aldehyde (Trade Name of IFF, 4(3)-(4-methyl-3-pentene-1-yl)-3-cyclohexene-1-carboxaldehyde), Lyral (Trade Name of IFF, 4(3)-(4-hydroxy-4-methylpentyl)-3-cyclohexene-1-carboxaldehyde), Cetonal (Trade Name of Givaudan, trimethyl cyclohexen methylbutanal), Vernaldehyde (Trade Name of Givaudan, 1-methyl-4-(4-methylpentyl)-3-cyclohexenecarbaldehyde), Melozone (Trade Name of IFF, octahydro-4,7-methanoindenecarboxaldehyde), Scentenal (Trade Name of Firmenich, methoxydicyclopentadienecarboxaldehyde), Dupical (Trade Name of Givaudan, 4-tricyclodecylidenebutanal), Bergamal (Trade Name of IFF, 3,7-dimethyl-2-methylene-6-octenal), campholenic aldehyde, Bourgeonal (Trade Name of Givaudan, 3-(4-tert-butylphenyl)propanal), Cyclamen Aldehyde (Trade Name of Givaudan, 3-(4-isopropylphenyl)-2-methylpropionaldehyde), Floralozone (Trade Name of IFF, 3-(4-ethylphenyl)-2,2-dimethylpropionaldehyde), Suzaral (Trade Name of Takasago International Corporation, 3-(4-isobutylphenyl)-2-methylpropionaldehyde), Lilyall (Trade Name of Givaudan, 3-(4-t-butylphenyl)-2-methyl propionaldehyde), Amyl Cinnamic Aldehyde (Trade Name of Kao Corporation), Hexyl Cinnamic Aldehyde (Trade Name of Kao Corporation), Canthoxal (Trade Name of IFF, 2-methyl-3-(4-methoxyphenyl)propanal), vanillin, ethyl vanillin, Heliotropine (Trade Name of Takasago International Corporation, 3,4-methylenedioxybenzaldehyde), Helional (Trade Name of IFF, alpha-methyl-1,3-benzodioxole-5-propanal), Triplal (Trade Name of IFF, 2,4-dimethyl-3-cyclohexene-1-carboxaldehyde), and 2,6-nonadienal. Among them, cis-4-decenal, Floral Super, Lyral, Cetonal, Scentenal, Dupical, Bourgeonal, Cyclamen Aldehyde, Floralozone, Suzaral, Lilyall, Amyl Cinnamic Aldehyde, Hexyl Cinnamic Aldehyde, Heliotropine, and Helional are preferable from the viewpoints of enhancing the sweetness and increasing the voluminousness by being blended with 2-n-pentyl cyclopentanone oxime.

Examples of ketones include methyl heptenone, dimethyl octenone, 3-octanone, hexylcyclopentanone, o-tert-butylcyclohexanone, dihydrojasmone, Veloutone (Trade Name of Firmenich, 2,2,5-trimethyl-5-pentylcyclopentanone), Nectaryl (Trade Name of Givaudan, 2-(2-(4-methyl-3-cyclohexen-1-yl)propyl)cyclopentanone), ionone, methylionone, gamma-methylionone, damascone, beta-damascone, delta-damascone, Isodamascone (Trade Name of Symrise, 1-(2,4,4-trimethyl-2-cyclohexyl)-trans-2-butanone), damascenone, Dynascone (Trade Name of Firmenich, 1-(5,5-dimethyl-1-cyclohexen-1-yl)-4-penten-1-one), Vetikon (Trade Name of Symrise, 4-methyl-4-phenylpentan-2-one), irone, Cashmeran (Trade Name of IFF, 1,2,3,5,6,7-hexahydro-1,1,2,3,3-pentamethyl-4H-inden-4-one), Iso E Super (Trade Name of IFF, 1-(1,2,3,4,5,6,7,8-octahydro-2,3,8,8-tetramethyl-2-naphthalenyl)-ethan-1-one), Calone (Trade Name of Firmenich, 7-methyl-3,4-dihydro-2H-benzodioxepin-3-one), carvone, menthone, acetyl cedrene, isolongifolanone, nootkatone, benzyl acetone, raspberry ketone, benzophenone, Tonalid (Trade Name of PFW, 6-acetyl-1,1,2,4,4,7-hexamethyl tetrahydronaphthalene), beta-methyl naphthyl ketone, ethyl maltol, camphor, muscone, Muscenone (Trade Name of Firmenich, 3-methyl-5-cyclopentadecen-1-one), civetone, and Globanone (Trade Name of Symrise, 8-cyclohexadecenone). Among them, hexylcyclopentanone, dihydrojasmone, Veloutone, damascone, beta-damascone, delta-damascone, Isodamascone, damascenone, benzyl acetone, benzophenone, and beta-methyl naphthyl ketone are preferable from the viewpoints of enhancing the sweetness and increasing the voluminousness by being blended with 2-n-pentyl cyclopentanone oxime.

Examples of acetals include Anthoxan (Trade Name of Kao Corporation), Boisambrene Forte (Trade Name of Kao Corporation, ethoxymethyl-cyclododecyl ether), Troenan (Trade Name of Kao Corporation, 5-methyl-5-propyl-2-(1-methylbutyl)-1,3-dioxane), Methyl Pamplemousse (Trade Name of Givaudan, 1,1-dimethoxy-2,2,5-trimethyl-4-hexene), phenylacetaldehyde dimethyl acetal, acetaldehyde ethyl linalyl acetal, citral dimethyl acetal, hydratropaldehyde dimethyl acetal, Verdoxan (Trade Name of Kao Corporation), and Floropal (Trade Name of Symrise, 2,4,6-trimethyl-4-phenyl-1,3-dioxane). Among them, Troenan, phenylacetaldehyde dimethyl acetal, acetaldehyde ethyl linalyl acetal, and Floropal are preferably from the viewpoints of enhancing the sweetness and increasing the voluminousness by being blended with 2-n-pentyl cyclopentanone oxime.

Examples of ethers include Herbavert (Trade Name of Kao Corporation), cedryl methyl ether, Ambroxan (Trade Name of Kao Corporation), Ambrotech (Trade Name of Kao Corporation), methyl isoeugenol, citronellyl ethyl ether, geranyl ethyl ether, 1,8-cineole, rose oxide, dihydro rose oxide, linalool oxide, estragole, anethole, hinokitiol, diphenyl oxide, beta-naphthol methyl ether, beta-naphthol ethyl ether, and Galaxolide (Trade Name of IFF, 1,3,4,6,7,8-hexahydro-4,6,6,7,8,8-hexamethylcyclopenta-gamma-2-benzopyran). Among them, citronellyl ethyl ether, geranyl ethyl ether, rose oxide, dihydro rose oxide, linalool oxide, diphenyl oxide, beta-naphthol methyl ether, and beta-naphthol ethyl ether are preferable from the viewpoints of enhancing the sweetness and increasing the voluminousness by being blended with 2-n-pentyl cyclopentanone oxime.

Examples of esters to be used as a fragrance material include aliphatic carboxylic acid ester, aromatic carboxylic acid ester, and other carboxylic acid esters.

Examples of aliphatic carboxylic acids that form aliphatic carboxylic acid ester include linear and branched carboxylic acids having 1 to 18 carbon atoms. Among them, carboxylic acids having 1 to 6 carbon atoms such as formic acid, acetic acid, glycolic acid, propionic acid, and butyric acid are important, and particularly acetic acid is important. Examples of aromatic carboxylic acids that form aromatic carboxylic acid ester include benzoic acid, anisic acid, phenylacetic acid, cinnamic acid, salicylic acid, phenyl glycidic acids, and anthranilic acids. Examples of alcohols that form aliphatic and aromatic esters include linear and branched aliphatic alcohols having 1 to 5 carbon atoms and the above-mentioned fragrance component alcohols.

Examples of other carboxylic acid esters include Ethyl Safranate (Trade Name of Givaudan, ethyl dihydrocyclo geranate), Poirenate (Trade Name of Kao Corporation), Fruitate (Trade Name of Kao Corporation, ethyl tricyclo [$5.2.1.0^{2.6}$] decan-2-carboxylate), methyl jasmonate, MDJ (Trade Name of Kao Corporation, methyl dihydrojasmonate), and tricyclodecenyl propionate. Among them, Ethyl Safranate, methyl jasmonate, and MDJ are preferable from the viewpoints of enhancing the sweetness and increasing the voluminousness by being blended with 2-n-pentyl cyclopentanone oxime.

Examples of carbonates include Liffarome (Trade Name of IFF, cis-3-hexenyl methyl carbonate), Jasmacyclat (Trade Name of Kao Corporation), and Floramat (Trade Name of Kao Corporation). Among them, Jasmacyclat and Floramat are preferable from the viewpoints of enhancing the sweetness and increasing the voluminousness by being blended with 2-n-pentyl cyclopentanone oxime.

Examples of lactones include gamma-nonalactone, gamma-decalactone, deltadecalactone, Jasmolactone (Trade Name of Firmenich, tetrahydro-6-(3-pentenyl)-2H-pyran-2-one), gamma-undecalactone, coumarin, octahydrocoumarin, Florex (Trade Name of Firmenich, 6-ethylideneoctahydro-5,8-methano-2H-1-benzopyran-2-one), cyclopentadecanolide, Habanolide (Trade Name of Firmenich, 12(11)-oxacyclohexadecen-2-one), Ambrettolide (Trade Name of IFF, 10-octacycloheptadecen-2-one), and ethylene bras sylate. Among them, Jasmolactone is preferable from the viewpoints of enhancing the sweetness and increasing the voluminousness by being blended with 2-n-pentyl cyclopentanone oxime.

Examples of oximes include Buccoxime (Trade Name of Symrise, 1,5-dimethyl-bicyclo[3,2,1]octan-8-one oxime), Labienoxime (Trade Name of Givaudan, 2,4,4,7-tetramethyl-6,8-nonadiene-3-one oxime), and 5-methyl-3-heptanone oxime.

Examples of nitriles include dodecanenitrile, citronellyl nitrile, cuminyl nitrile, cinnamyl nitrile, and Peonile (Trade Name of Givaudan, 2-cyclohexylidene-2-phenylacetonitrile). Among them, Peonile is preferable from the viewpoints of enhancing the sweetness and increasing the voluminousness by being blended with 2-n-pentyl cyclopentanone oxime.

Examples of Schiff bases include Aurantiol (Trade Name of Givaudan, methyl N-(3,7-dimethyl-7-hydroxyoctylidene)-anthranilate), Ligantral (Trade Name of Givaudan, methyl (3,5-dimethyl-3-cyclohexene-1-yl)methyleneanthranilate), and methyl 2-[(2-methylundecylidene)amino]benzoate. Among them, Aurantiol and Ligantral are preferable from the viewpoints of enhancing the sweetness and increasing the voluminousness by being blended with 2-n-pentyl cyclopentanone oxime.

Examples of amides include Gardamide (Trade Name of Givaudan, N,2-dimethyl-N-phenylbutyramide) and Paradisamide (Trade Name of Givaudan, 2-ethyl-N-methyl-N-(3-methylphenyl)butanamide).

Examples of other nitrogen-containing compounds include pyrroles, indoles, and thiazoles. Among them, indoles are preferable from the viewpoints of enhancing the sweetness and increasing the voluminousness by being blended with 2-n-pentyl cyclopentanone oxime.

Examples of the sulfur-containing compounds include thiols, sulfides, thiophenes, thiocarboxylic acids, and cyclic thioethers.

Examples of the natural essential oils and the natural extracts include orange, lemon, lime, bergamot, petitgrain, neroli, vanilla, mandarin, peppermint, spearmint, lavender, lavandin, chamomile, rosemary, *eucalyptus*, sage, basil, rose, rockrose, geranium, jasmine, ylang ylang, anise, clove, ginger, nutmeg, cardamon, cedar wood, cypress, vetiver, guaiac wood, patchouli, lemongrass, labdanum, *galbanum*, olibanum, and gurjun balsam. Among them, neroli, lavender, lavandin, chamomile, rosemary, rose, rockrose, geranium, jasmine, and ylang ylang are preferable from the viewpoints of enhancing the sweetness and increasing the voluminousness by being blended with 2-n-pentyl cyclopentanone oxime.

The amount of these other fragrances to be contained can be selected suitably depending on, for example, the type of the blended fragrance as well as the type and intensity of intended odor. However, from the viewpoints of enhancing the sweetness and increasing the voluminousness of the fragrance composition, the amount of each of them contained in the fragrance composition is preferably 0.0001 to 99.99 mass %, more preferably 0.001 to 80 mass %, and the total amount of them contained in the fragrance composition is preferably 5 to 99.99 mass %, more preferably 50 to 99.9 mass %.

The fragrance composition of the present invention also provides effects of further enhancing the sweetness and increasing the voluminousness in addition to the odor of 2-n-pentyl cyclopentanone oxime. Such a fragrance composition can be used suitably to provide fragrances for cleanser compositions, fabric treatment compositions, cosmetics, etc.

<Use as Fragrance Component>

The fragrance composition containing 2-n-pentyl cyclopentanone oxime of the present invention can be used, as a fragrance component for various types of products, as a blended fragrance that has green floral and fruity like odors and that is excellent in fragrance retention. Therefore, the present invention provides a method of using 2-n-pentyl cyclopentanone oxime as a fragrance component, preferably a method of using 2-n-pentyl cyclopentanone oxime as a fragrance component for a fragrance composition, a cleanser composition, a fabric treatment composition, or a cosmetic. For the specific method of using said compound, it can be contained, alone or in combination with other components, in the bases of toiletry products such as soaps, cosmetics, detergents, softeners, spray products, air fresheners, perfumes, and bath agents.

Particularly, since the 2-n-pentyl cyclopentanone oxime contained in the fragrance composition of the present invention has green floral and fruity like odors, it is preferable to be used, as a fragrance component, for cleanser compositions, fabric treatment compositions, or cosmetics. Since it is excellent in fragrance retention, it is preferable to be used for cleanser compositions.

Accordingly, the present invention also provides a cleanser composition, a fabric treatment composition such as a softener composition, and a cosmetic that each contain a fragrance composition of the present invention.

As described above, the fragrance composition of the present invention has sweetness and voluminousness. Even when, for example, an activator and an oil are blended additionally to the fragrance composition of the present invention, it has an odor intensity equivalent to that of the fragrance composition itself of the present invention and enhances the odor. Therefore, the fragrance composition of the present invention is used preferably for cleanser compositions, fabric treatment compositions, and cosmetics and is used more preferably for cleanser compositions.

The cleanser composition of the present invention is preferably a body cleanser composition, a cleanser composition for clothing, or a cleanser composition for hard surfaces, more preferably a body cleanser composition or a cleanser composition for clothing, and further preferably a body cleanser composition.

Examples of the body cleanser composition include a skin cleanser composition and a hair cleanser composition. It is preferably a skin cleanser composition.

Examples of the cleanser composition for hard surfaces include an all purpose cleaner and a cleanser composition for tableware.

The fabric treatment composition of the present invention is preferably a softener composition.

The cosmetic of the present invention is preferably a perfume.

It is preferable that the cleanser composition of the present invention contain an anionic surfactant in addition to 2-n-pentyl cyclopentanone oxime or a fragrance composition containing 2-n-pentyl cyclopentanone oxime of the present invention. Furthermore, a nonionic surfactant, a pH adjuster, a viscosity modifier, a solvent, an oil, a preservative, water, etc. can be blended thereinto.

It is preferable that the softener composition of the present invention contain a cationic surfactant in addition to 2-n-pentyl cyclopentanone oxime or a fragrance composition containing 2-n-pentyl cyclopentanone oxime of the present invention. Furthermore, a pH adjuster, a solvent, an oil, a preservative, water, etc. can be blended thereinto.

In the perfume of the present invention, a solvent, water, etc. can be blended thereinto in addition to 2-n-pentyl cyclopentanone oxime or a fragrance composition containing 2-n-pentyl cyclopentanone oxime of the present invention.

As described above, 2-n-pentyl cyclopentanone oxime has green floral and fruity like odors and is excellent in fragrance retention. Therefore, as described above, the present invention provides a method of using 2-n-pentyl cyclopentanone oxime as a fragrance component, for example, as a fragrance component for a fragrance composition, a cleanser composition, a fabric treatment composition, or a cosmetic. The cleanser composition is preferably a body cleanser composition, a cleanser composition for clothing, or a cleanser composition for hard surfaces, more preferably a body cleanser composition or a cleanser composition for clothing, and further preferably a body cleanser composition. Examples of the body cleanser composition include skin cleanser compositions and hair cleanser compositions, and it is preferably a skin cleanser composition. Examples of the cleanser composition for hard surfaces include all purpose cleaners and cleanser compositions for tableware. The fabric treatment composition is preferably a softener composition. The cosmetic is preferably a perfume.

In the above-mentioned method of using 2-n-pentyl cyclopentanone oxime, 2-n-pentyl cyclopentanone oxime is used in an amount of preferably 0.01 to 99 mass %, more preferably 0.1 to 50 mass %, and further preferably 0.3 to 25 mass % with respect to the whole subject (for example, a fragrance composition, a cleanser composition, a fabric treatment composition, or a cosmetic) to be imparted with an odor from the view point of enhancing the sweetness and voluminousness of the fragrance composition.

In the above-mentioned method of using 2-n-pentyl cyclopentanone oxime, 2-n-pentyl cyclopentanone oxime is used in an amount of preferably 0.01 to 99 mass %, more preferably 0.1 to 50 mass %, and further preferably 0.3 to 25 mass % with respect to the whole subject (for example, a fragrance composition, a cleanser composition, a fabric treatment composition, or a cosmetic) to be imparted with an odor, since 2-n-pentyl cyclopentanone oxime enhances the sweetness and the voluminousness and furthermore maintains the odor intensity and enhances the odor even when an activator, an oil, etc. are blended additionally therewith.

In the above-mentioned method of using 2-n-pentyl cyclopentanone oxime, the fragrance composition containing 2-n-pentyl cyclopentanone oxime used as a fragrance component may contain an oil, which itself has no odor. The oil is the same as that described with respect to the fragrance composition. Furthermore, in the above-mentioned method of using 2-n-pentyl cyclopentanone oxime, the fragrance composition containing 2-n-pentyl cyclopentanone oxime used as a fragrance component may contain, as another fragrance, another fragrance component that is commonly used or a blended fragrance with a desired composition in addition to 2-n-pentyl cyclopentanone oxime. Examples of such another fragrance are the same as those described with respect to the fragrance composition.

In the above-mentioned method of using 2-n-pentyl cyclopentanone oxime, a cleanser composition, a fabric treatment composition, or a cosmetic, in which 2-n-pentyl cyclopentanone oxime is used as a fragrance component, may contain an oil, which itself has no odor. The oil is the same as that described with respect to the fragrance composition. Furthermore, in the above-mentioned method of using 2-n-pentyl cyclopentanone oxime, a subject (for example, a cleanser composition, a fabric treatment composition, or a cosmetic) to be imparted with an odor, in which 2-n-pentyl cyclopentanone oxime is used as a fragrance component, may contain, as another fragrance, another fragrance component that is commonly used or a blended fragrance with a desired composition in addition to 2-n-pentyl cyclopentanone oxime. Examples of such another fragrance are the same as those described with respect to the fragrance composition.

<Method of Producing 2-n-Pentyl Cyclopentanone Oxime>

The 2-n-pentyl cyclopentanone oxime that is used in the present invention can be synthesized utilizing a general organic chemical reaction and the method of producing it is not limited. A preferable method of producing 2-n-pentyl cyclopentanone oxime is a method of producing it by a step of oximating 2-n-pentyl cyclopentanone.

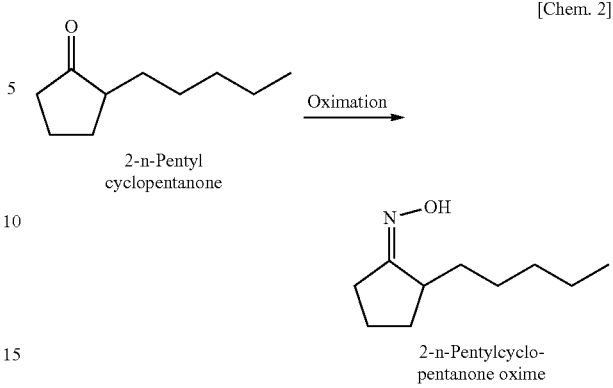

[Chem. 2]

2-n-Pentyl cyclopentanone 2-n-Pentylcyclopentanone oxime 2-n-pentyl cyclopentanone can be prepared according to known documents. Examples of available commercial products of 2-n-pentyl cyclopentanone include Delphone (Trade Name, manufactured by Firmenich).

<Oximation Step>

A suitable method to be employed in this step is preferably a method of mixing 2-n-pentyl cyclopentanone and hydroxylamine. Specific examples thereof include a method of dropping a hydroxylamine aqueous solution into 2-n-pentyl cyclopentanone, a method of dropping 2-n-pentyl cyclopentanone into a hydroxylamine aqueous solution, and a method of dropping a base into a mixture of 2-n-pentyl cyclopentanone and an aqueous solution of inorganic acid salt of hydroxylamine. Among them, the method of dropping a base into a mixture of 2-n-pentyl cyclopentanone and an aqueous solution of inorganic acid salt of hydroxylamine is preferable. With this method, dropping a base can result in free hydroxylamine generated in the reaction system and as a result, side reactions can be inhibited and thus the reaction can be carried out safely.

The inorganic acid salt of hydroxylamine used in this step is preferably hydroxylamine sulfate or hydroxylamine hydrochloride from the viewpoints of inhibition of the side reactions and economic efficiency and is more preferably hydroxylamine sulfate from the viewpoints of yield and selectivity.

From the viewpoints of simplicity in the post-reaction treatment and economic efficiency, the amount of the hydroxylamine or an inorganic acid salt thereof to be used is, in terms of hydroxylamine, preferably 0.8 to 3.0 times by mole, more preferably 0.8 to 2.0 times by mole, and further preferably 0.8 to 1.5 times by mole, with respect to 2-n-pentyl cyclopentanone.

The base used in the suitable method of dropping a base is one of stronger bases than hydroxylamine and particularly it is preferably water soluble. From an economic perspective, it is preferably alkali metal hydroxide such as sodium hydroxide or potassium hydroxide. From the viewpoints of handleability and operating efficiency, it is preferable to use an aqueous solution containing 20 to 50 mass % of alkali metal hydroxide.

The oximation reaction can be carried out in the absence of a solvent. However, from the viewpoint of inhibiting the increase in viscosity of the reaction solution that is caused by gradual heating and the development of the reaction, it is preferable to use a solvent. The solvent is preferably water or aliphatic alcohol that easily dissolves ingredients, namely 2-n-pentyl cyclopentanone and hydroxylamine, and is more preferably water. The aliphatic alcohol is preferably aliphatic alcohol having 1 to 3 carbon atoms, more preferably linear aliphatic alcohol having 1 to 3 carbon atoms, and further preferably, for example, ethanol or isopropyl alcohol. The above-mentioned solvent is preferably water or a mixture of aliphatic alcohol and water, more preferably water, and further preferably water alone.

From the viewpoint of inhibiting the increase in viscosity of the reaction solution that is caused by gradual heating and the development of the reaction, when hydroxylamine or an inorganic acid salt thereof is used, the amount of the solvent to be used is preferably 0.5 to 10 times by mass, more preferably 1 to 5 times by mass, and further preferably 2 to 4 times by mass, with respect to the hydroxylamine or inorganic acid salt thereof. Furthermore, from the viewpoint of inhibiting the increase in viscosity of the reaction solution that is caused by gradual heating and the development of the reaction, the amount of the solvent to be used is preferably 0.1 to 5 times by mass, more preferably 0.5 to 3 times by mass, and further preferably 1 to 2 times by mass, with respect to 2-n-pentyl cyclopentanone.

From the viewpoints of completing the reaction efficiently and inhibiting exothermic decomposition of hydroxylamine, it is preferable that the reaction temperature be maintained at 20 to 60 degrees C.

From the viewpoints of improving the quality of the 2-n-pentyl cyclopentanone oxime, which is obtained by this step, so that it has a more preferable quality as a fragrance material, it is preferable that the solvent and a byproduct with a high boiling point be removed by, for example, distillation purification.

Furthermore, 2-n-pentyl cyclopentanone oxime may be produced according to a method described in, for example, N. Radulovic, et al., Food and Chemical Toxicology, 2012, vol. 50, pp. 274-279.

Moreover, the present invention provides a method of producing a fragrance composition containing 2-n-pentyl cyclopentanone oxime, wherein the method includes a step of oximating 2-n-pentyl cyclopentanone to obtain 2-n-pentyl cyclopentanone oxime and a step of mixing an oil and/or a fragrance other than 2-n-pentyl cyclopentanone oxime with 2-n-pentyl cyclopentanone oxime. In the step of oximating 2-n-pentyl cyclopentanone to obtain 2-n-pentyl cyclopentanone oxime, it is preferable to use a solvent.

With respect to the above-mentioned embodiment, the present invention further discloses the following method of producing 2-n-pentyl cyclopentanone oxime, fragrance composition, cleanser composition, fabric treatment composition, cosmetic, and method of using 2-n-pentyl cyclopentanone oxime.

<1> A fragrance composition, containing 2-n-pentyl cyclopentanone oxime.

<2> The fragrance composition according to the item <1>, wherein the amount of the 2-n-pentyl cyclopentanone oxime contained in the fragrance composition is preferably 0.01 to 99 mass %, more preferably 0.1 to 50 mass %, and further preferably 0.3 to 25 mass %.

<3> The fragrance composition according to the item <1> or <2>, further containing a fragrance in addition to the 2-n-pentyl cyclopentanone oxime.

<4> The fragrance composition according to any one of the items <1> to <3>, further containing an oil.

<5> The fragrance composition according to any one of the items <1> to <4>, wherein the amount of the oil contained in the fragrance composition is preferably 0.01 to 95 mass %, more preferably 1 to 90 mass %, and further preferably 5 to 80 mass %.

<6> The fragrance composition according to any one of the items <3> to <5>, wherein the fragrance contained in addition to the 2-n-pentyl cyclopentanone oxime contains at least one selected from hydrocarbons, alcohols, phenols, aldehydes, ketones, acetals, ethers, esters, carbonates, lactones, oximes, nitriles, Schiff bases, amides, nitrogen-containing compounds, sulfur-containing compounds, natural essential oils, and natural extracts.

<7> The fragrance composition according to any one of the items <3> to <6>, wherein the fragrance contained in addition to the 2-n-pentyl cyclopentanone oxime contains at least one selected from fragrances having respective fragrance notes of a citrus tone, a floral tone, a fruity tone, a herbal tone, a spicy tone, a green tone, a woody tone, a balsamic tone, an aldehydic tone, a minty tone, an aromatic tone, an earthy tone, a mossy tone, a honey tone, a leather tone, an animalic tone, an amber tone, and a musky tone.

<8> A cleanser composition containing a fragrance composition according to any one of the items <1> to <7>.

<9> A fabric treatment composition containing a fragrance composition according to any one of the items <1> to <7>.

<10> A cosmetic containing a fragrance composition according to any one of the items <1> to <7>.

<11> A method of using 2-n-pentyl cyclopentanone oxime as a fragrance component, preferably as a fragrance component for a fragrance composition, a cleanser composition (preferably a body cleanser composition (for example, a skin cleanser composition, a hair cleanser composition, and preferably a skin cleanser composition), a cleanser composition for clothing, or a cleanser composition for hard surfaces (for example, an all purpose cleaner and a cleanser composition for tableware), more preferably a body cleanser composition or a cleanser composition for clothing, and further preferably a body cleanser composition), a fabric treatment composition (preferably a softener composition), or a cosmetic (preferably a perfume).

<12> The method of using 2-n-pentyl cyclopentanone oxime according to the item <11>, wherein the 2-n-pentyl cyclopentanone oxime is used in an amount of preferably 0.01 to 99 mass %, more preferably 0.1 to 50 mass %, and further preferably 0.3 to 25 mass % with respect to the whole subject (for example, a fragrance composition, a cleanser composition, a fabric treatment composition, or a cosmetic) to be imparted with an odor.

<13> The method of using 2-n-pentyl cyclopentanone oxime according to the item <11> or <12>, wherein further an oil is used.

<14> The method of using 2-n-pentyl cyclopentanone oxime according to the item <13>, wherein the oil is used in an amount of preferably 0.01 to 95 mass %, more preferably 1 to 90 mass %, and further preferably 5 to 80 mass % with respect to the whole subject (for example, a fragrance composition, a cleanser composition, a fabric treatment composition, or a cosmetic) to be imparted with an odor.

<15> The method of using 2-n-pentyl cyclopentanone oxime according to any one of the items <11> to <14>, wherein further a fragrance other than the 2-n-pentyl cyclopentanone oxime is used as a fragrance component.

<16> The method of using 2-n-pentyl cyclopentanone oxime according to the item <15>, wherein the fragrance other than the 2-n-pentyl cyclopentanone oxime contains at least one selected from hydrocarbons, alcohols, phenols, aldehydes, ketones, acetals, ethers, esters, carbonates, lactones, oximes, nitriles, Schiff bases, amides, nitrogen-containing compounds, sulfur-containing compounds, natural essential oils, and natural extracts.

<17> The method of using 2-n-pentyl cyclopentanone oxime according to the item <15> or <16>, wherein the fragrance other than the 2-n-pentyl cyclopentanone oxime contains at least one selected from fragrances having respective fragrance notes of a citrus tone, a floral tone, a fruity tone, a herbal tone, a spicy tone, a green tone, a woody tone, a balsamic tone, an aldehydic tone, a minty tone, an aromatic tone, an earthy tone, a mossy tone, a honey tone, a leather tone, an animalic tone, an amber tone, and a musky tone.

<18> A method of producing a fragrance composition containing 2-n-pentyl cyclopentanone oxime, including a step of oximating 2-n-pentyl cyclopentanone to obtain 2-n-pentyl cyclopentanone oxime and a step of mixing an oil and/or a fragrance other than 2-n-pentyl cyclopentanone oxime with 2-n-pentyl cyclopentanone oxime.

<19> The method of producing a fragrance composition containing 2-n-pentyl cyclopentanone oxime according to the item <18>, wherein a solvent (for example, aliphatic alcohol or water) is used for an oximation reaction.

<20> The method of producing a fragrance composition according to the item <18> or <19>, wherein the oximation is carried out by mixing 2-n-pentyl cyclopentanone and hydroxylamine or an inorganic acid salt thereof, and the amount of the solvent is preferably 0.5 to 10 times by mass, more preferably 1 to 5 times by mass, and further preferably 2 to 4 times by mass, with respect to the hydroxylamine or inorganic acid salt thereof.

<21> The method of producing a fragrance composition according to any one of the items <18> to <20>, wherein the oximation is carried out by mixing 2-n-pentyl cyclopentanone and hydroxylamine or an inorganic acid salt thereof, and the amount of the solvent is preferably 0.1 to 5 times by mass, more preferably 0.5 to 3 times by mass, and further preferably 1 to 2 times by mass, with respect to the 2-n-pentyl cyclopentanone.

<22> A method of producing 2-n-pentyl cyclopentanone oxime, including a step of oximating 2-n-pentyl cyclopentanone in the presence of a solvent (for example, aliphatic alcohol or water) to obtain 2-n-pentyl cyclopentanone oxime.

<23> The method of producing 2-n-pentyl cyclopentanone oxime according to the item <22>, wherein the oximation is carried out by mixing 2-n-pentyl cyclopentanone and hydroxylamine or an inorganic acid salt thereof, and the amount of the solvent is preferably 0.5 to 10 times by mass, more preferably 1 to 5 times by mass, and further preferably 2 to 4 times by mass, with respect to the hydroxylamine or inorganic acid salt thereof.

<24> The method of producing 2-n-pentyl cyclopentanone oxime according to the item <22> or <23>, wherein the oximation is carried out by mixing 2-n-pentyl cyclopentanone and hydroxylamine or an inorganic acid salt thereof, and the amount of the solvent is preferably 0.1 to 5 times by mass, more preferably 0.5 to 3 times by mass, and further preferably 1 to 2 times by mass, with respect to the 2-n-pentyl cyclopentanone.

EXAMPLES

The following examples further describe and demonstrate embodiments of the present invention. The examples are given solely for the purpose of illustration and are not to be construed as limitations of the present invention.

Details of the measurement methods carried out in the following examples and comparative examples are described together below.

Details of the measurement methods carried out in the following production examples are described together below.

<Conversion Ratio and Reaction Yield>

The conversion ratios and the reaction yields described in the following production examples were determined by an internal standard method of gas chromatography (GC) quantitative analysis.

<Apparatus and Analytical Conditions for Gas Chromatography>

GC Apparatus: HP6850, manufactured by HEWLETT PACKARD

Column: DB-1 (Inner Diameter: 0.25 mm, Length: 30 m, and Film Thickness: 0.25 micrometer), manufactured by J&W Carrier Gas: He, 1.5 mL/min Injection Condition: 280 degrees C., Split Ratio: 1/100

Detection Condition: FID System, 280 degrees C.

Column Temperature Condition: Raised from 100 degrees C. to 300 degrees C. at 10 degrees C./min then maintained at 300 degrees C. for 10 minutes Internal Standard Compound: n-Undecane <Compound Identification>

Each compound obtained in the following production examples was identified by spectrum analyses using a nuclear magnetic resonance spectrum (Mercury 400, manufactured by Varian) ($^1$H-NMR, $^{13}$C-NMR) and a Fourier transform infrared spectrophotometer (FT-710, manufactured by HORIBA, Ltd.). The measurement conditions, etc. are described in each measurement result.

<Odor Evaluation of Fragrance Composition>

One expert who had an experience of at least five years but less than ten years as well as two experts who had an experience of at least 25 years of blending odors and evaluating fragrances determined the fragrance note and the intensity by a smelling strip method. About 5 mm of the end of each smelling strip (fragrance test paper with a width of 6 mm and a length of 150 mm) was immersed in a sample and thereby evaluation was performed.

With respect to the odor, fragrances that are sensed mainly (main odors) were listed from the strongest to the weakest and further fragrances that are sensed secondarily (secondary odors) were noted.

The odor intensity was indicated by the relative evaluation, with 0 denoting odorless and 5 denoting very strong.

<Evaluation of Fragrance Retention>

As in the case of the above-mentioned smelling strip method, a strip was immersed in a sample and then was left in a 5 m$^3$ windless room at 25 degrees C. It was evaluated every six hours and the time when the odor intensity of the main odor became zero was indicated. The longer the time, the better the fragrance retention.

<Evaluation of Fragrance Notes of Cleanser Composition, Fabric Treatment Composition, and Cosmetic>

One expert who had an experience of at least five years but less than ten years as well as two experts who had an experience of at least 25 years of blending odors and evaluating fragrances evaluated the fragrance note of the odor at the mouth of the bottle.

Production Example 1

Production of 2-n-Pentyl Cyclopentanone Oxime

[Chem. 3]

Amylcyclopentanone → 2-n-Pentylcyclopentanone oxime

In a 1 L separable flask, 354 g of ion exchanged water, 140 g of hydroxylamine sulfate (0.84 mole, 1.05 times by mole with respect to ketone in terms of hydroxylamine), and 250 g of amyl cyclopentanone (2-n-pentyl cyclopentanone, Delphone manufactured by Firmenich, 1.60 moles) were added sequentially. This mixture was heated to 45 degrees C. while being stirred in a nitrogen atmosphere. While the reaction temperature was kept at 45 degrees C. to 55 degrees C., 140 g of 48 mass % sodium hydroxide aqueous solution (1.68 moles, 2.00 times by mole with respect to hydroxylamine sulfate) was dropped to the mixture over one hour. After completion of dropping, heating and stirring were continued at 50 degrees C. for 23 hours. After completion of the reaction, an aqueous layer was extracted by settled separation. With ion exchanged water added thereto, it then was washed at 50 degrees C. Thus, 278 g of crude product of colorless viscous liquid was obtained. As a result of gas chromatography quantitative analysis of the crude product, a conversion ratio of amyl cyclopentanone was 99.2% and 2-n-pentyl cyclopentanone oxime had a pure content of 263 g (1.55 moles), a purity of 95.0%, and a crude yield of 97.0%.

Then 170 g of the crude product was subjected to vacuum distillation purification and thereby 159 g of colorless viscous fraction that was distilled at 114 to 121 degrees C./0.40 to 0.54 kPa was obtained. The fraction had a pure content of 155 g (0.92 mole) of 2-n-pentyl cyclopentanone oxime and a purity of 2-n-pentyl cyclopentanone oxime was 97.2%.

The measurement results of each spectrum analysis of 2-n-pentyl cyclopentanone oxime are indicated below.

[Math.1]

(1) $^1$H-NMR (CDCl$_3$, 400 MHz); δ (ppm): 0.88 (3H, t, J=6.8 Hz), 1.22-1.42 (8H, m), 1.51-1.66 (1H, m), 1.66-1.76 (1H, m), 1.76-1.90 (1H, m), 1.94-2.02 (1H, m), 2.32-2.50 (2H, m), 2.55-2.63 (1H, m), 9.29 (1H, S).

(2) $^{13}$C-NMR (CDCl$_3$, 100 MHz); δ (ppm): 14.5, 22.9, 23.0, 27.7, 27.8, 32.1, 32.3, 32.6, 43.6, 169.3.

(3) FT-IR (neat); cm$^{-1}$: 725, 846, 919, 954, 1197, 1376, 1421, 1461, 1677, 2856, 2925, 2954, 3257 (br).

(4) Odor: Main Odor: Green-floral (*Magnolia*); Secondary Odor: Fruity.

(5) Odor Intensity: 3.

Production Example 2

In a 1 L separable flask, 138 g of hydroxylamine sulfate (0.83 mole, 1.30 times by mole with respect to ketone in terms of hydroxylamine), 406 g of ion exchanged water, 129 g of isopropyl alcohol, 198 g of amyl cyclopentanone (2-n-pentyl cyclopentanone, Delphone manufactured by Firmenich, 1.28 moles) were added sequentially. This mixture was heated to 45 degrees C. while being stirred in a nitrogen atmosphere. While the reaction temperature was kept at 45 degrees C. to 55 degrees C., 185 g of 33 mass % sodium hydroxide aqueous solution (1.53 moles, 1.84 times by mole with respect to hydroxylamine sulfate) was dropped to the mixture over one hour. After completion of dropping, heating and stirring were continued at 50 degrees C. for 4.5 hours. After completion of the reaction, an aqueous layer was neutralized with a 1 mole/L sulfuric acid aqueous solution and 300 g of ethyl acetate was added thereto. Thus, extraction was carried out. The aqueous layer was extracted by settled separation and then was washed with saturated saline. An organic layer was dried with sodium sulfate and then was filtered. After that, the solvent was evaporated to dryness under reduced pressure and thereby 220 g of crude product of colorless viscous liquid was obtained. As a result of gas chromatography quantitative analysis of the crude product, a conversion ratio of amyl cyclopentanone was 99.8% and a pure content of 2-n-pentyl cyclopentanone oxime was 211 g (1.24 moles), a purity of 2-n-pentyl cyclopentanone oxime was 95.5%, and a crude yield of 2-n-pentyl cyclopentanone oxime was 96.8%.

Then 220 g of this crude product was subjected to vacuum distillation purification and thereby 212 g of colorless viscous fraction that was distilled at 115 to 121 degrees C./0.13 to 0.16 kPa was obtained. The fraction had a pure content of 210 g (1.24 moles) of 2-n-pentyl cyclopentanone oxime and a purity of 2-n-pentyl cyclopentanone oxime was 99.0%.

Production Example 3

Production of 2-n-Hexylcyclopentanone Oxime 2-n-Hexylcyclopentanone oxime was obtained in the same manner as in Production Example 1 except for using 2-n-hexylcyclopentanone instead of amyl cyclopentanone.

The measurement results of each spectrum analysis are indicated below.

[Math.2]

(1) $^1$H-NMR (CDCl$_3$, 400 MHz); δ (ppm): 0.88 (3H, t, J=6.8 Hz), 1.22-1.42 (10H, m), 1.52-1.66 (1H, m), 1.66-1.77 (1H, m), 1.77-1.92 (1H, m), 1.94-2.02 (1H, m), 2.31-2.52 (2H, m), 2.54-2.63 (1H, m), 9.02 (1H, S).

(2) $^{13}$C-NMR (CDCl$_3$, 100 MHz); δ (ppm): 14.6, 22.9, 23.1, 27.7, 28.0, 29.8, 32.1, 32.2, 32.6, 43.6, 169.4.

(3) FT-IR (neat); cm$^{-1}$: 723, 919, 960, 1207, 1376, 1421, 1455, 1670, 2856, 2925, 2954, 3276 (br).

Production Example 4

Production of 2-n-Heptyl Cyclopentanone Oxime 2-n-Heptyl cyclopentanone oxime was obtained in the same manner as in Production Example 1 except for using 2-n-heptyl cyclopentanone instead of amyl cyclopentanone.

The measurement results of each spectrum analysis are indicated below.

[Math.3]

(1) $^1$H-NMR (CDCl$_3$, 400 MHz); δ (ppm): 0.88 (3H, t, J=6.8 Hz), 1.20-1.42 (12H, m), 1.52-1.66 (1H, m), 1.66-1.77 (1H, m), 1.77-1.92 (1H, m), 1.94-2.02 (1H, m), 2.31-2.52 (2H, m), 2.54-2.63 (1H, m), 8.99 (1H, S).

(2) $^{13}$C-NMR (CDCl$_3$, 100 MHz); δ (ppm): 14.6, 23.0, 23.1, 27.7, 28.1, 29.7, 30.1, 32.1, 32.3, 32.7, 43.6, 169.4.
(3) FT-IR (neat); cm$^{-1}$: 723, 919, 964, 1205, 1376, 1421, 1455, 1673, 2854, 2921, 2954, 3286 (br).

<Odor Evaluation Results for Compounds Obtained in Production Examples 1, 3, and 4 as Well as Fragrance Composition Containing Amyl Cyclopentanone>

The compound obtained in Production Example 1 was dissolved in dipropylene glycol at a concentration of 90 mass % and thereby a fragrance composition of Example 1 was prepared. Thereafter, it was subjected to the odor evaluation by the aforementioned odor evaluation method. Using, instead of the compound obtained in Production Example 1, the compound obtained in Production Example 3, the compound obtained in Production Example 4, or amyl cyclopentanone (Delphone, manufactured by Fimenich), the same procedure as in Example 1 was carried out. Thus a composition of Comparative Example 1, Comparative Example 2, or Comparative Example 3 was obtained. With respect to the compositions of Comparative Example 1, Comparative Example 2, and Comparative Example 3 thus obtained, the odor evaluation was carried out in the same manner as in the case of the composition of Example 1. Table 1 shows the results thus obtained.

TABLE 1

| | Ex. 1 | C. Ex. 1 | C. Ex. 2 | C. Ex. 3 |
|---|---|---|---|---|
| Compound | 2-n-Pentyl cyclopentanone oxime | 2-n-Hexyl cyclopentanone oxime | 2-n-Heptyl cyclopentanone oxime | 2-n-Pentyl cyclopentanone (amyl cyclopentanone) |
| Structure | NOH, C$_5$H$_{11}$ | NOH, C$_6$H$_{13}$ | NOH, C$_7$H$_{15}$ | O, C$_5$H$_{11}$ |
| Intensity | 3 | 3 | 2 | 4 |
| Main Odor | Green-Fluoral | Green | Green | Fruity |
| Secondary Odor | Fruity | Floral | Floral | Floral |
| Fragrance Retention | 10 Days | Woody At least 10 days | Woody At least 10 days | 18 Hours |

The fragrance composition containing 2-n-pentyl cyclopentanone oxime of the present invention was different in its odor from the other oxime compounds of Comparative Examples 1 and 2 as well as the fragrance composition containing 2-n-pentyl cyclopentanone of Comparative Example 3, and had green floral and fruity like odors. Furthermore, the fragrance composition containing 2-n-pentyl cyclopentanone oxime of the present invention was also excellent in fragrance retention as compared to the fragrance composition containing 2-n-pentyl cyclopentanone of Comparative Example 3.

Example 2 and Comparative Examples 4, 5, and 6

Fragrance Composition with Fruity (Peach) Tone

Using the 2-n-pentyl cyclopentanone oxime obtained in Production Example 1, fragrances each were prepared in such a manner as to have a mixed composition indicated in Table 2. Thus, fragrance compositions with a fruity (peach) tone of Example 2 and Comparative Examples 4, 5, and 6 were prepared, respectively.

TABLE 2

| Fruity (Peach) Tone Fragrance Composition | Ex. 2 | C. Ex. 4 | C. Ex. 5 | C. Ex. 6 |
|---|---|---|---|---|
| γ-Undecalactone | 100 | 100 | 100 | 100 |
| Ethyl 3-methyl-phenylglycidate | 5 | 5 | 5 | 5 |
| Aurantiol[1] | 5 | 5 | 5 | 5 |
| β-Damascone | 1.5 | 1.5 | 1.5 | 1.5 |
| Benzyl acetate | 50 | 50 | 50 | 50 |
| Benzyl salicylate | 150 | 150 | 150 | 150 |
| cis-3-Hexenol | 1.5 | 1.5 | 1.5 | 1.5 |
| Methyl N-methylanthranilate | 5 | 5 | 5 | 5 |
| Ethyl butyrate | 1.5 | 1.5 | 1.5 | 1.5 |
| Ethylene brassylate | 150 | 150 | 150 | 150 |
| Geraniol | 15 | 15 | 15 | 15 |
| Hexyl cinnamic aldehyde | 100 | 100 | 100 | 100 |
| Indole | 0.1 | 0.1 | 0.1 | 0.1 |
| Lemon oil | 20 | 20 | 20 | 20 |
| Triplal[2] | 3 | 3 | 3 | 3 |
| Linalool | 100 | 100 | 100 | 100 |
| Linalool oxide | 3 | 3 | 3 | 3 |
| MDJ[3] | 150 | 150 | 150 | 150 |
| Orange oil | 50 | 50 | 50 | 50 |
| o-tert-Butylcyclohexyl acetate | 30 | 30 | 30 | 30 |
| Prenyl acetate | 5 | 5 | 5 | 5 |
| Vanillin | 1.5 | 1.5 | 1.5 | 1.5 |

(Unit: Part by Mass)

TABLE 2-continued

| Fruity (Peach) Tone Fragrance Composition | Ex. 2 | C. Ex. 4 | C. Ex. 5 | C. Ex. 6 |
|---|---|---|---|---|
| 2-Methyl-4-propyl-1,3-oxathiane | 0.2 | 0.2 | 0.2 | 0.2 |
| 2-n-Pentyl cyclopentanone oxime | 20 | 0 | 0 | 0 |
| Magnol[4] | 0 | 20 | 0 | 0 |
| Buccoxime[5] | 0 | 20 | 0 | 0 |
| Dipropylene glycol | 32.7 | 32.7 | 32.7 | 52.7 |
| Total | 1000 | 1000 | 1000 | 1000 |

(Unit: Part by Mass)

[1]Trade Name of Givaudan, Methyl N-(3,7-dimethyl-7-hydroxyoctylidene)-anthranilate
[2]Trade Name of IFF, 2,4-Dimethyl-3-cyclohexene-1-carboxaldehyde
[3]Trade Name of Kao Corporation, Methyl dihydrojasmonate
[4]Trade Name of Kao Corporation, Isomer mixture containing, for example, (4-ethyl-bicyclo[2.2.1]hept-2-yl)cyclohexanol and (2-ethyl-bicyclo[2.2.1]hept-7-yl)cyclohexanol.
[5]Trade Name of Symrise, 1,5-dimethyl-bicyclo[3,2,1]octan-8-one oxime Evaluation was performed in the same manner as in the aforementioned odor evaluation. Table 3 shows the results.

TABLE 3

| Odor Evaluation | Ex. 2 | C. Ex. 4 | C. Ex. 5 | C. Ex. 6 |
|---|---|---|---|---|
| Main Odor | Fruity | Fruity | Fruity | Fruity |
| Secondary Odor | Green | Floral | Herbal | Floral |
| Intensity of Main Odor | 4 | 4 | 4 | 3 |
| Fragrance Retention of Sweetness and Voluminousness | 2 Days | None | None | None |
| Effect | Green fruitiness of peach and sweetness are enhanced. Odor volume and intensity are increased. Harmonious natural fragrance is formed. | Fragrance is monotonous and darker. Muguet like odor is enhanced, which causes imbalance. | Cassis like odor is enhanced and thereby sense of herb is increased, which resulted in unclean fragrance. | Simple peach like odor. |

The fragrance composition of Example 2 was different in the secondary odor from Comparative Examples 4, 5, and 6 and had an enhanced peach skin like green sweetness and formed a more natural fragrance. Furthermore, as compared to the fragrance composition of Comparative Example 6, the fragrance composition of Example 2 had not only enhanced intensity but also enhanced fragrance retention of sweetness and voluminousness and thereby the effect thereof was maintained for a longer time.

Example 3 and Comparative Examples 7, 8, and 9

Concentrated Liquid Softener Composition

To a non-fragranced concentrated liquid softener composition with the composition indicated in Table 4, the fragrance compositions obtained in Example 2 and Comparative Examples 4, 5, and 6 each were added to be contained at 1.0 mass %. Thus, concentrated liquid softener compositions of Example 3 and Comparative Examples 7, 8, and 9 were prepared, respectively.

TABLE 4

| Non-Fragranced Concentrated Liquid Softener Composition | Blended Amount (mass %) |
|---|---|
| Quaternary cationic softener base[1] | 16.6 |
| 20% Magnesium chloride hexahydrate | 0.2 |
| Preservative[2] | 0.1 |
| Ion exchanged water | Remainder |
| pH | 3.5 |

[1]Trade Name of Kao Corporation: Tetranyl L1/90S
[2]Trade Name of Lonza: Lonzaserve SG Evaluation was performed by the method of evaluating the fragrance notes of the cleanser composition, the fabric treatment composition, and the cosmetic. Table 5 shows the results.

TABLE 5

| Odor Evaluation | Ex. 3 | C. Ex. 7 | C. Ex. 8 | C. Ex. 9 |
|---|---|---|---|---|
| Main Odor | Fruity | Fruity | Fruity | Fruity |
| Secondary Odor | Green | Floral | Herbal | Floral |
| Main Odor Intensity | 4 | 3 | 4 | 3 |
| Fragrance Retention of Sweetness and Voluminousness | 2 Days | None | None | None |
| Effect | As in the fragrance composition, green fruitiness of peach and sweetness are enhanced. Odor volume and intensity are increased. Harmonious natural fragrance is formed. | As compared to the fragrance composition, fragrance becomes further monotonous and also had decreased fragrance intensity. Floral like odor of the secondary odor is enhanced, which causes imbalance. | As compared to the fragrance composition, the sense of herb further is enhanced, which makes the cassis like odor main. Thus, sense of peach is weakened considerably. | Simple peach like odor. |

As compared to the softener composition of Comparative Example 9, the softener composition of Example 3 had an enhanced peach skin like green sweetness and thereby formed a more natural fragrance. Furthermore, the softener composition of Example 3 had enhanced fragrance retention of sweetness and voluminousness and thereby the effect thereof was maintained for a longer time.

Example 4 and Comparative Example 10

Fragrance Composition with Floral (Orange Flower) Tone

Using the 2-n-pentyl cyclopentanone oxime obtained in Production Example 1, fragrances each were prepared in such a manner as to have a mixed composition indicated in Table 6. Thus, fragrance compositions with a floral (orange flower) tone of Example 4 and Comparative Example 10 were prepared, respectively.

TABLE 6

| Floral (Orange Flower) Tone Fragrance Composition | Ex. 4 | C. Ex. 10 |
|---|---|---|
| | (Unit: Part by Mass) | |
| Benzyl acetate | 15 | 15 |
| Citronellol | 50 | 50 |
| Ethyl linalyl acetate | 75 | 75 |
| Geraniol | 100 | 100 |
| Indole | 2.5 | 2.5 |
| MDJ[1] | 200 | 200 |
| Methyl anthranilate | 10 | 10 |
| β-Methyl naphthyl ketone | 25 | 25 |
| Nerolidol | 25 | 25 |
| Phenethyl alcohol | 150 | 150 |
| Tetrahydrolinalool | 75 | 75 |
| Nerol | 0 | 50 |
| 2-n-Pentyl cyclopentanone oxime | 50 | 0 |
| Dipropylene glycol | 222.5 | 222.5 |

TABLE 6-continued

| Floral (Orange Flower) Tone Fragrance Composition | Ex. 4 | C. Ex. 10 |
|---|---|---|
| | (Unit: Part by Mass) | |
| Total | 1000 | 1000 |

[1]Trade Name of Kao Corporation, Methyl dihydrojasmonate

Evaluation was performed in the same manner as in the aforementioned odor evaluation. As compared to the fragrance composition of Comparative Example 10, the fragrance composition of Example 4 had an enhanced sense of green and sweetness of orange flower as well as increased voluminousness as a whole.

Example 5 and Comparative Example 11

(Skin Cleanser Composition (Body Wash))

To a non-fragranced skin cleanser composition (body wash) with the composition indicated in table 7, the fragrance compositions obtained in Example 4 and Comparative Example 10 each were added to be contained at 0.5 mass %. Thus, skin cleanser compositions (body wash) of Example 5 and Comparative Example 11 were prepared, respectively.

TABLE 7

| Non-Fragranced Skin Cleanser Composition (Body Wash) | Blended Amount (mass %) |
|---|---|
| Sodium polyoxyethylene(2)lauryl ether sulfate | 9.1 |
| Polyethoxyethylenated alcohol | 6.4 |
| Linear fatty acid | 2.9 |
| Citric acid | 3.0 |
| 50% Sodium hydroxide | 2.8 |
| Ethanol | 1.0 |
| Preservative | 0.15 |
| Sodium chloride | Suitable Amount |
| Ion exchanged water | Remainder |
| pH | 8.3 |

1) Trade Name of Kao Corporation: Emal 227
2) Trade Name of Kao Corporation: Betadet HR
3) Trade Name of Kao Corporation: Amidet B-112
4) Trade Name of Lonza: Isocil PC Evaluation was performed by the method of evaluating the fragrance notes of the cleanser composition, the fabric treatment composition, and the cosmetic. As compared to the skin cleanser composition (body wash) of Comparative Example 11, the skin cleanser composition (body wash) of Example 5 had enhanced sense of green and sweetness of orange flower as well as increased voluminousness as a whole.

[Example 6 and Comparative Example 12] (Fragrance Composition with Floral (*Magnolia*) Tone)

Using the 2-n-pentyl cyclopentanone oxime obtained in Production Example 1, fragrances each were prepared in such a manner as to have a mixed composition indicated in Table 8. Thus, fragrance compositions with a floral (*magnolia*) tone of Example 6 and Comparative Example 12 were prepared, respectively.

TABLE 8

| Floral (Magnolia) Tone Fragrance Composition | Ex. 6 | C. Ex. 12 |
|---|---|---|
| | (Unit: Part by Maas) | |
| Y-Undecalactone | 3 | 3 |
| Amber Core[1] | 20 | 20 |
| Benzyl acetate | 50 | 50 |
| Boisambrene Forte[2] | 10 | 10 |
| cis-3-Hexenyl salicylate | 10 | 10 |
| Florosa[3] | 100 | 100 |
| Galvanum oil | 0.1 | 0.1 |
| Indole | 0.3 | 0.3 |
| Jasmine Absolute | 5 | 5 |
| Lemon oil | 10 | 10 |
| MDJ[4] | 150 | 150 |
| β-Methyl naphthyl ketone | 5 | 5 |
| Neroli oil | 10 | 10 |
| Phenethyl alcohol | 100 | 100 |
| Tetrahydrolinalool | 150 | 150 |
| Triplal[5] | 3 | 3 |
| Troenan[6] | 10 | 10 |
| 2-n-Pentyl cyclopentanone oxime | 15 | 0 |
| Dipropylene glycol | 248.6 | 263.6 |
| Total | 1000 | 1000 |

[1]Trade Name of Kao Corporation, 1-(2-tert-Butyl cyclohexyloxy)-2-butanol
[2]Trade Name of Kao Corporation, Ethoxymethyl cyclododecyl ether
[3]Trade Name of Givaudan, 4-Methyl-2-(2-methylpropyl)tetrahydro-2H-4-pyranol
[4]Trade Name of Kao Corporation, Methyl dihydrojasmonate
[5]Trade Name of IFF, 2,4-Dimethyl-3-cyclohexene-1-carboxaldehyde
[6]Trade Name of Kao Corporation, 5-Methyl-5-propyl-2-(1-methylbutyl)-1,3-dioxane Evaluation was performed in the same manner as in the aforementioned odor evaluation. As compared to the fragrance composition of Comparative Example 12, the fragrance composition of Example 6 had enhanced sense of green and fruitiness of *magnolia*, formed a more natural fragrance, and had enhanced sweetness. Furthermore, voluminousness was added to the whole fragrance.

Example 7 and Comparative Example 13

(Hair Cleanser Composition (Shampoo))

To a non-fragranced hair cleanser with the composition indicated in Table 9, the fragrance compositions obtained in Example 6 and Comparative Example 12 each were added to be contained at 0.5 mass %. Thus, hair cleanser compositions of Example 7 and Comparative Example 13 were prepared, respectively.

TABLE 9

| Non-Fragranced Hair Cleanser (Shampoo) | Blended Amount (mass %) |
|---|---|
| Sodium polyoxyethylene(2)lauryl sulfate[1] | 14.7 |
| Cocamide propyl betaine[2] | 10.0 |
| Cocamide diethanol amide[3] | 1.5 |
| Sodium chloride | 0.3 |
| Preservatives[4] | 0.1 |
| 20% Citric acid | Suitable Amount |
| 0.1% Sodium hydroxide | Suitable Amount |
| Ion exchanged water | Remainder |
| pH | 6 |

[1]Trade Name of Kao Corporation: Emal 227
[2]Trade Name of Kao Corporation: Betadet HR
[3]Trade Name of Kao Corporation: Amidet B-112
[4]Trade Name of Lonza: Isocil PC Evaluation was performed by the method of evaluating the fragrance notes of the cleanser composition, the fabric treatment composition, and the cosmetic. As compared to the hair cleanser composition of Comparative Example 13, the hair cleanser composition of Example 7 had enhanced sense of green and fruitiness of *magnolia*, formed a more natural fragrance, and had enhanced sweetness. Furthermore, voluminousness was added to the whole fragrance.

Example 8 and Comparative Example 14

Fragrance Composition with Woody (Vetiver) Tone

Using the 2-n-pentyl cyclopentanone oxime obtained in Production Example 1, fragrances each were prepared in such a manner as to have a mixed composition indicated in Table 10. Thus, fragrance compositions with a woody (vetiver) tone of Example 8 and Comparative Example 14 were prepared, respectively.

TABLE 10

| Woody (Vetiver) Tone Fragrance Composition | (Unit: Part by Mass) | |
|---|---|---|
| | Ex. 8 | C. Ex. 14 |
| Acetyl cedrene | 100 | 100 |
| Cedar wood oil | 100 | 100 |
| Guaiac wood oil | 50 | 50 |
| Gurjun balsam oil | 100 | 100 |
| o-tert-Butylcyclohexanone | 1 | 1 |
| p-tert-Butylcyclohexanol | 15 | 15 |
| p-tert-Butylcyclohexyl acetate | 75 | 75 |
| Thiazyl 1% in DPG[1] | 0.25 | 0.25 |
| Vetikon[2] | 25 | 25 |
| 2-n-Pentyl cyclopentanone oxime | 150 | 0 |
| Dipropylene glycol | 383.75 | 533.75 |
| Total | 1000 | 1000 |

[1]Trade Name of PFW: 2-Isobutylthiazole (1% Dipropylene glycol solution)
[2]Trade Name of Symrise: 4-Methyl-4-phenylpentan-2-one Evaluation was performed in the same manner as in the aforementioned odor evaluation. As compared to the fragrance composition of Comparative Example 14, the fragrance composition of Example 8 had enhanced sweetness and a distinctive sense of vetiver. The 2-n-pentyl cyclopentanone oxime made the component forming the woody tone distinctive, and the voluminousness also was increased.

Example 9 and Comparative Example 15

Perfume

The fragrance compositions obtained in Example 8 and Comparative Example 14 each were added to ethanol to be contained at 10 mass %. Thus, perfumes of Example 9 and Comparative Example 15 were prepared, respectively.

Evaluation was performed in the same manner as in the aforementioned odor evaluation. As compared to the perfume of Comparative Example 15, the perfume of Example 9 had enhanced sweetness and distinctive sense of vetiver. The 2-n-pentyl cyclopentanone oxime made the component forming the woody tone distinctive, and the voluminousness also was increased.

INDUSTRIAL APPLICABILITY

Since 2-n-pentyl cyclopentanone oxime has green floral and fruity like odors, which are useful as fragrances, the fragrance composition containing 2-n-pentyl cyclopentanone oxime of the present invention can be used as a fragrance material. Furthermore, the fragrance composition containing 2-n-pentyl cyclopentanone oxime of the present invention is excellent in fragrance retention and can enhance the sweetness and increase the voluminousness by being blended with another fragrance.

As described above, the fragrance composition containing 2-n-pentyl cyclopentanone oxime of the present invention can be used as a fragrance component for a cleanser composition, a fabric treatment composition, a cosmetic, etc.

The invention may be embodied in other forms without departing from the spirit or essential characteristics thereof. The embodiments disclosed in this application are to be considered in all respects as illustrative and not limiting. The scope of the invention is indicated by the appended claims rather than by the foregoing description, and all changes which come within the meaning and range of equivalency of the claims are intended to be embraced therein.

The invention claimed is:

1. A method of imparting a fragrance to a fragrance composition, a cleanser composition, a fabric treatment composition, or a cosmetic, said method comprising adding 2-n-pentyl cyclopentanone oxime to said fragrance composition, cleanser composition, fabric treatment composition, or cosmetic.

2. A method according to claim 1, wherein said fragrance composition, cleanser composition, fabric treatment composition, or cosmetic comprises 2-n-pentyl cyclopentanone oxime in an amount of 0.01 to 99 mass % with respect to the total mass of the fragrance composition, cleanser composition, fabric treatment composition, or cosmetic.

3. A method according to claim 1, wherein said fragrance composition, cleanser composition, fabric treatment composition, or a cosmetic comprises 2-n-pentyl cyclopentanone oxime in an amount of 0.1 to 50 mass % with respect to the total mass of the fragrance composition, cleanser composition, fabric treatment composition, or cosmetic.

4. A method according to claim 1, wherein the fragrance composition, cleanser composition, fabric treatment composition, or a cosmetic comprises another compound capable of imparting fragrance other than 2-n-pentyl cyclopentanone oxime.

5. A fragrance composition comprising 2-n-pentyl cyclopentanone oxime and another fragrance compound in addition to the 2-n-pentyl cyclopentanone oxime.

6. A fragrance composition according to claim 5, further comprising an oil.

7. A fragrance composition according to claim 6, wherein said oil present in the fragrance composition is present in an amount of from 0.01 to 95 mass %.

8. A fragrance composition according to claim 6, wherein said oil present in the fragrance composition is present in an amount of from 1 to 90 mass %.

9. A fragrance composition according to claim 5, wherein said another fragrance compound comprises at least one member selected from the group consisting of a hydrocarbon, an alcohol, a phenol, an aldehyde, a ketone, an acetal, an ether, an ester, a carbonate, a lactone, an oxime, a nitriles, a Schiff base, an amide, a nitrogen-containing compound, a sulfur-containing compound, a natural essential oil, and a natural extract.

10. A fragrance composition according to claim 5, wherein said another fragrance compound comprises at least one member selected from the group consisting of a fragrance having respective fragrance notes of a citrus tone, a floral tone, a fruity tone, a herbal tone, a spicy tone, a green tone, a woody tone, a balsamic tone, an aldehydic tone, a minty tone, an aromatic tone, an earthy tone, a mossy tone, a honey tone, a leather tone, an animalic tone, an amber tone, and a musky tone.

11. A method according to claim 1, wherein said method imparts a fragrance to a cleanser composition.

12. A method according to claim 11, wherein said cleanser composition is a skin cleanser composition.

13. A method according to claim 11, wherein said cleanser composition is a hair cleanser composition.

14. A method according to claim 1, wherein said method imparts a fragrance to a fabric treatment composition.

15. A method according to claim 14, wherein said fabric treatment composition is a softener composition.

16. A method according to claim 1, wherein said method imparts a fragrance to a cosmetic.

17. A method of producing a fragrance composition comprising 2-n-pentyl cyclopentanone oxime,
the method comprising:
oximating 2-n-pentyl cyclopentanone to provide 2-n-pentyl cyclopentanone oxime, and
mixing at least one of an oil and another fragrance compound other than 2-n-pentyl cyclopentanone oxime with 2-n-pentyl cyclopentanone oxime.

18. A method according to claim 17, wherein a solvent is present during said oximating.

19. A method according to claim 18, wherein said oximating is carried out by mixing 2-n-pentyl cyclopentanone and hydroxylamine or an inorganic acid salt thereof, and the amount of the solvent is 0.5 to 10 times by mass with respect to the hydroxylamine or inorganic acid salt thereof.

20. A method according to claim 18, wherein said oximating is carried out by mixing 2-n-pentyl cyclopentanone and hydroxylamine or an inorganic acid salt thereof, and the amount of the solvent is 0.1 to 5 times by mass with respect to the 2-n-pentyl cyclopentanone.

\* \* \* \* \*